United States Patent [19]

Querou

[11] 4,309,550

[45] Jan. 5, 1982

[54] BENZOXAZOLONE PREPARATION

[75] Inventor: Yvon Querou, Nanterre, France

[73] Assignee: Rhone-Poulenc Agrochimie, Lyons, France

[21] Appl. No.: 143,859

[22] Filed: Apr. 25, 1980

[30] Foreign Application Priority Data

May 8, 1979 [FR] France .................................. 79 12140

[51] Int. Cl.$^3$ .......................................... C07D 263/58
[52] U.S. Cl. .................................................. 548/221
[58] Field of Search ........................................ 548/221

[56] References Cited

U.S. PATENT DOCUMENTS 3,812,138  5/1974  Heise et al. .......................... 548/165

FOREIGN PATENT DOCUMENTS 1269067  7/1961  France ................................. 548/221
2048270 12/1980  United Kingdom ................ 548/221

OTHER PUBLICATIONS

Wagner et al., "Synthetic Organic Chemistry", (1951), pp. 665-666.

Primary Examiner—Anton H. Sutto
Attorney, Agent, or Firm—Burns, Doane, Swecker & Mathis

[57] ABSTRACT

Benzoxazolone is prepared by heating ortho-chlorophenol under superatmospheric ammonia pressure, and thence by adding urea to the medium of reaction and continuing the heating of same, but under atmospheric pressure.

23 Claims, No Drawings

BENZOXAZOLONE PREPARATION

CROSS-REFERENCE TO RELATED APPLICATION

My copending application, Ser. No. 143,857, filed concurrently herewith, and hereby expressly incorporated by reference in its entirety and relied upon.

BACKGROUND OF THE INVENTION

1. Field of the Invention

The present invention relates to the preparation of benzoxazolone from a phenol, and, more especially, to the preparation of benzoxazolone from chlorophenol.

2. Description of the Prior Art

Benzoxazolone is a known compound having the structural formula:

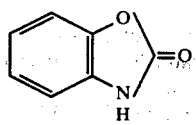

Such known compound is a useful intermediate in the synthesis of a variety of other materials, e.g., the insecticide phosalone. An benzoxazolone is ofttimes designated benzoxazolinone, in particular in the English speaking countries.

It too is known to prepare benzoxazolone by fairly diverse methods, beginning with rather exotic reactants. Compare, for example, French Pat. No. 1,269,067. Also compare U.S. Pat. No. 3,812,138.

SUMMARY OF THE INVENTION

Accordingly, a major object of the present invention is the provision of a simple and facile process for the preparation of benzoxazolone, starting with simple reactants and, more particularly, utilizing ortho-chlorophenol as the primary reactant.

Briefly, the present invention features the preparation of benzoxazolone from ortho-chlorophenol, comprising, in a first step, heating ortho-chlorophenol under positive ammonia pressure, and then, in a second distinct step, adding urea to the mixture of reaction resulting from said first step, and thence continuing heating said medium of reaction under atmospheric pressure, preferably in the presence of water.

DETAILED DESCRIPTION OF THE INVENTION

More particularly according to this invention, in a preferred embodiment, the first step of the subject process is carried out in the presence of a metal catalyst; a copper-based catalyst is advantageously employed for this purpose. Exemplary of such catalysts are cuprous or cupric salts, in particular the halides, sulfates, phosphates, acetates, propionates and acetylacetonates (cuprous chloride is preferred), and also the oxides (in particular cuprous oxide), and copper metal; the catalysts comprising iron or nickel are also envisaged.

The amount of catalyst present in the reaction medium is generally between 0.5 and 20%, preferably between 2 and 10%, by weight, relative to the ortho-chlorophenol. However, while amounts of catalysts without these ranges can indeed be used, such would not constitute any significant advantage, economic or otherwise.

The first reaction step is also carried out under ammonia pressure. In other words, the subject process comprises heating a liquid reaction medium under a pressurized atmosphere which includes ammonia gas. Preferably, the NH₃ is added, under pressure, to the atmosphere surmounting or enveloping the reaction medium. The total pressure is advantageously between 1 and 60 bars (relative pressures), preferably between 3 and 40 bars. Higher pressures, e.g., ranging up to 150 bars, can also be used.

In the aforementioned atmosphere comprising ammonia and surmounting the reaction medium in the first step, the ammonia gas (NH₃) is preferably essentially in pure state, but it can also be at a partial pressure of more than 50% of the total pressure or, preferably, of more than 90% of this pressure. Said ammonia gas is most frequently supplied from either an external feed, or results from prior introduction thereof into the reactor, or from a combination of these factors. The temperature of the reaction medium, in the first step, is advantageously between 100° and 250° C., preferably between 140° and 230° C.

This first reaction step can also be carried out in the presence of inert inorganic or organic solvents, but, generally, it is preferably carried out in bulk. Such bulk reaction mixture is typically liquid, in particular at the temperature of reaction.

The duration of this first reaction step can obviously vary, depending upon the operating conditions. Simple routine experiments will enable those skilled in the art to determine the optimum duration; generally, this first reaction step is continued until the ortho-chlorophenol content of the reaction admixture is no longer varying to any significant extent, or, stated differently, until the degree of conversion of the ortho-chlorophenol has essentially reached its maximum, not taking into account simple thermal and/or chemical degradation.

As heretofore indicated, the process of the invention comprises two reaction steps; in fact, these two steps are separate and distinct, in particular by reason of the fact that the first is carried out under positive pressure while the second is simply carried out under atmospheric pressure. However, apart from this distinction, these two steps are fairly similar from a practical point of view and same can conveniently be carried out one after the other or sequentially, simply by means of a small change in the operating conditions and by introducing the urea before the second step, but without same being truly necessary, between the two reaction steps, e.g., to transfer the reaction medium to another reactor or to subject same to certain particular treatments. This reflects that, despite the ostensible inclusion of two distinct reaction steps, the process of the invention is indeed very simple and very convenient to carry out. This simplicity and this convenience are virtually tantamount to a process strictly comprising but a single reaction step.

The second reaction step is carried out under atmospheric pressure, preferably in a vessel open to the atmosphere and upon the introduction of the urea. In view of the volatility of ammonia, heating under atmospheric pressure is equivalent to heating in the total or virtually total absence of ammonia. However, a small amount of ammonia can be present, especially due to the decomposition of the urea to at least some extent, but even in this case the ammonia readily evolves from the reaction medium under the influence of the heat. The molar ratio of the urea employed in the second step of the reaction, to the ortho-chlorophenol (initial amounts), is typically between 1 and 15, preferably between 1.2 and 8. The reaction temperature during this second step is typically between 80° and 220° C., preferably between 110° and 190° C.

This second reaction step, moreover, is preferably carried out in the presence of water. However, in view of the temperature and the pressure, the water tends to evaporate more or less rapidly, such that, in accordance with another embodiment of the invention, liquid water is continuously fed into the reaction medium and, if appropriate, the steam leaving the reaction medium is recovered and condensed. In accordance with these procedures, water is advantageously fed into the reaction medium at a rate per hour which is less than 20% by weight of the reaction medium. Upon completion of the reaction, the benzoxazolone is isolated and recovered by any means iself known to the art. According to a preferred and quite advantageous operational technique, the benzoxazolone is precipitated with water which may itself be acidified; the benzoxazolone can be purified by any known means, e.g., by recrystallization or by washing with an organic solvent.

The process of the invention is especially worthwhile because of the good results obtained, both as regards the degree of conversion of the ortho-chlorophenol and the yields of benzoxazolone, and also in respect of the simplicity and the convenience with which the process is carried out.

In order to further illustrate the present invention and the advantages thereof, the following specific examples are given, it being understood that same are intended only as illustrative and in nowise limitative. In the examples which follow, DC denotes the degree of conversion of the ortho-chlorophenol and Y denotes the yield of benzoxazolone, relative to the ortho-chlorophenol converted.

EXAMPLE 1

Ortho-chlorophenol (12.85 g) and $Cu_2O$ (0.715 g) were introduced into a 125 cc stainless steel autoclave equipped with stirring means.

The autoclave was purged with ammonia, and ammonia ($NH_3$) (14.7 g) was then introduced. The autoclave was heated at 140° C. for 8 hours. The pressure stabilized at 40 bars upon commencement of the heating and at 20 bars upon termination of the heating. The autoclave was cooled to 125° C. and the ammonia was permitted to escape. Urea (6.12 g) and water (1 g) were added and the autoclave was then heated, at atmospheric pressure, at 140° C. for 2 hours and then at 150° C. for 2 hours (at the same pressure). Same was cooled to 120° C. and a 1 N aqueous solution of HCl (100 cc) was added. The precipitated benzoxazolone was filtered off and was obtained in a Y of 53% and a DC of 65%.

EXAMPLE 2

Ortho-chlorophenol (12.85 g) and $Cu_2Cl_2$ (0.99 g) were introduced into the same apparatus as employed in Example 1.

The autoclave was purged with ammonia, and ammonia (27 g) was then introduced. The autoclave was heated at 170° C. for 3 hours, the pressure being about 120 bars. The autoclave was cooled to 125° C. and the ammonia was permitted to escape; urea (5.4 g) and water (1 g) were introduced. By following the procedure of Example 1, the benzoxazolone was then obtained in a Y of 67% and a DC of 69%.

EXAMPLE 3

Example 2 was repeated, but the autoclave was heated at 170° C. for 8 hours (instead of 3 hours) and 7.7 g of urea (instead of 5.4 g) were introduced; the benzoxazolone was thus obtained in a Y of 70% and a DC of 93%.

EXAMPLE 4

Ortho-chlorophenol (7.2 g) and cuprous chloride (0.28 g) were introduced into a 140 cc autoclave lined on the inside with polytetrafluoroethylene.

The autoclave was sealed and purged with $NH_3$, and $NH_3$ (7 g) was introduced. The autoclave was heated at 180° C. for 6 hours. The pressure initially stabilized at about 40 bars (relative pressure) and then gradually declined to about 26 bars upon completion of the reaction.

The autoclave was cooled to 120° C. and opened and urea (16.8 g) and water (0.6 cc) were then added. Without distillation, the autoclave was heated under atmospheric pressure for 2 hours at 150° C. and then for 2 hours at 180° C. It as cooled to 120° C., a 1 N aqueous solution of hydrochloric acid (60 cc) was added, the autoclave was cooled to 20° C. and extraction was carried out with ethyl acetate. In the organic phase, the benzoxazolone was obtained in a Y of 56% and a DC of 99%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of benzoxazolone, comprising, in a first step, heating ortho-chlorophenol at an elevated temperature under superatmospheric ammonia pressure until the degree of conversion of the ortho-chlorophenol has essentially stabilized, and thence, in a second step, adding urea to the medium of reaction and continuing heating same at an elevated temperature, but under atmospheric pressure.

2. The process as defined by claim 1, wherein the pressure in the first step ranges from 1 to 60 bars.

3. The process as defined by claim 2, wherein the pressure in the first step ranges from 3 to 40 bars.

4. The process as defined by claim 2, wherein the partial pressure of the ammonia comprising the first step superatmospheric pressure is in excess of 50% of the total pressure.

5. The process as defined by claim 4, wherein the said partial pressure of the ammonia is in excess of 90% of the total pressure.

6. The process as defined by claim 1 of 4, wherein the molar ratio of the urea added to the initial ortho-chlorophenol ranges from 1 to 15.

7. The process as defined by claim 6, wherein said ratio urea/ortho-chlorophenol ranges from 1.2 to 8.

8. The process as defined by claim 6, wherein the medium of reaction is heated in the first step to a temperature ranging from 100° to 250° C.

9. The process as defined by claim 8, wherein the medium of reaction is heated in the first step to a temperature ranging from 140° to 230° C.

10. The process as defined by claim 8, wherein the medium of reaction is heated in the second step to a temperature ranging from 80° to 220° C.

11. The process as defined by claim 1, wherein the medium of reaction is heated in the second step to a temperature ranging from 110° to 190° C.

12. The process as defined by claim 10, wherein the heating of the medium of reaction is conducted in the presence of water, at least in the second heating step.

13. The process as defined by claim 1, wherein the heating of the medium of reaction is conducted in the presence of a metal catalyst.

14. The process as defined by claim 13, wherein the metal catalyst is a copper catalyst.

15. The process as defined by claim 14, wherein the copper catalyst is a cuprous salt.

16. The process as defined by claim 15, wherein the cuprous salt is cuprous chloride.

17. The process as defined by claims 13 or 14, wherein the amount of catalyst in the medium of reaction ranges from 0.5 to 20% by weight, based upon the weight of the ortho-chlorophenol.

18. The process as defined by claim 17, wherein the amount of catalyst ranges from 2 to 10% by weight, based upon the weight of the ortho-chlorophenol.

19. The process as defined by claim 12, the water comprising less than 20% by weight of the medium of reaction.

20. The process as defined by claim 1, the first step being conducted in an inert solvent.

21. The process as defined by claim 1, wherein the second step is conducted under conditions of distillation.

22. The process as defined by claim 14, said catalyst being selected from the group consisting of copper metal, copper oxide, and cuprous or cupric halide, sulfate, phosphate, acetate, propionate and acetylacetonate.

23. The process as defined by claim 13, wherein the metal catalyst is an iron or nickel catalyst.

* * * * *